United States Patent [19]
Kuzmak

[11] Patent Number: 5,910,149
[45] Date of Patent: Jun. 8, 1999

[54] NON-SLIPPING GASTRIC BAND

[76] Inventor: Lubomyr I. Kuzmak, 30 Crest Dr., South Orange, N.J. 07079

[21] Appl. No.: 09/067,918

[22] Filed: Apr. 29, 1998

[51] Int. Cl.$^6$ ................................................. A61B 17/04
[52] U.S. Cl. ........................................... 606/157; 606/151
[58] Field of Search .................... 606/151, 157; 600/29–31

[56] References Cited

U.S. PATENT DOCUMENTS

| | | |
|---|---|---|
| 4,592,339 | 6/1986 | Kuzmak et al. . |
| 4,696,288 | 9/1987 | Kuzmak et al. . |
| 5,074,868 | 12/1991 | Kuzmak et al. .................. 606/157 |
| 5,226,429 | 7/1993 | Kuzmak et al. .................. 128/898 |
| 5,449,368 | 9/1995 | Kuzmak et al. .................. 606/157 |
| 5,601,604 | 2/1997 | Vincent et al. .................. 606/216 |

Primary Examiner—Gary Jackson
Attorney, Agent, or Firm—Larson & Taylor

[57] ABSTRACT

A securing or holding element is incorporated into a gastric band to prevent slippage or migration of the gastric band after installation thereof around the stomach to restrict the size of a stoma opening. The securing element includes laterally extending, perforate end portions which are adapted to be secured by suturing to stomach tissue adjacent to the gastric band. The end portions of the securing element can be folded over onto the gastric band to reduce the cross sectional profile presented, and thus facilate introduction into the patient of the gastric band and securing element through a laparoscopic cannula during a laparoscopic procedure employing the band.

5 Claims, 2 Drawing Sheets

NON-SLIPPING GASTRIC BAND

FIELD OF THE INVENTION

The present invention relates to gastric banding devices which are used in the treatment of morbid obesity and which, in use, encircle a portion of the stomach to form a stoma opening of reduced diameter so as to restrict food intake and, more particularly, to an improved gastric banding device which combats or minimizes slippage of the device when in place.

BACKGROUND OF THE INVENTION

Gastric banding devices of the general type discussed above, which are also referred to as, depending on the characteristics thereof, stoma adjustable silicone gastric banding ("SASGB") devices or stoma laparoscopic adjustable placement ("SLAP") gastric band devices, are described in a number of patents including U.S. Pat. Nos. 5,449,368 (Kuzmak), 5,226,429 (Kuzrnak), 5,074,868 (Kuzmak), 4,696,288 (Kuzmak, et al.) and 4,592,339 (Kuzmak, et al.) and the references cited therein. While reference is made to these patents for a more complete description of these device in general, gastric bands of this type are introduced in the body, either by open wound surgery or, preferably, by a laparoscopic procedure, and secured in place around the stoma opening by various means described in the above patents and in other prior art. The bands include an inflatable or expandable section which encircles the stoma opening and which can be controlled by a remote reservoir or fill port, normally sutured to the body, to adjust the size of this opening.

Although these gastric bands have been highly successful (in European countries, in particular), there have been occasions where a problem has occurred with slippage of the band over time, i.e., with migration of the band within the body from the site around the stoma opening at which the band was initially placed and secured, e.g., by suturing. It will be appreciated that such slippage or migration is undesirable and in an extreme case could cause medical complications.

SUMMARY OF THE INVENTION

In accordance with the invention, an improved gastric band of the general type discussed above is provided which incorporates means for positively holding or securing the band in place so as to substantially reduce or prevent slippage or migration of the band after placement of the band around the stomach and thus overcome the problems with prior art gastric bands discussed above. The holding means of the invention is particularly adapted for laparoscopic band placement and, to this end, the holding means can be compacted in size, prior to use, so as to reduce the cross section presented by the combination of the band and holding means, thereby facilitating introduction of the combination into the body through a laparoscopic cannula. After introduction, the holding means is expanded to serve its holding or securing function, i.e., so that a portion or portions thereof can be secured to the adjacent tissue, e.g., by suturing. An important feature of the holding means is that at least part of the securing portions of the holding means are formed of a mesh material or other perforate material so that tissue can grow therethrough and assist in holding the gastric band in place.

According to a preferred embodiment of the invention, there is provided, in combination, (1) a gastric band adapted for laparoscopic placement around the stomach of a patient so as to control the size of the stomach opening and (2) holding means for holding the gastric band in place around the stomach, the gastric band comprising a band member having a proximal end and a distal end, means for joining or connecting the distal end to an intermediate part of the band member so as to form a looped portion including an inner stomach-facing surface, a fluid reservoir, an inflatable member located on the inner surface of the looped portion, and fluid communication means, extending between the inflatable member and the distal end of the band member, for providing fluid communication between the inflatable member and the reservoir so as to enable inflation of the inflatable member from the reservoir, and the holding means comprising at least one elongate holding element secured to the band member and extending transversely to the band member, the at least one holding element including oppositely directed free end portions, the free end portions being movable between a first position wherein the holding element is used to hold the gastric band in place and wherein the free end portions extend beyond the band member on opposite sides thereof so as to enable said free end portions to be affixed to stomach tissue of the patient adjacent to the band member and a second position wherein the holding element and the band member are adapted to be inserted through a laparoscopic cannula and wherein the free end portions are folded over onto the band member so as to decrease the cross sectional profile presented by the holding element and band member.

Preferably, as set forth above, at least the free end portions of the holding element comprise perforate members.

If so required to provide the necessary holding or securing forces, the holding means advantageously comprises a plurality of said holding elements.

Other features and advantages of the invention will be set forth in, or apparent from, the following detailed description of preferred embodiments of the invention.

BRIEF DESCRIPTIONS OF THE DRAWINGS

DETAILED DESCRIPTION OF THE PREFERRED EMBODIMENTS

Figure 1:
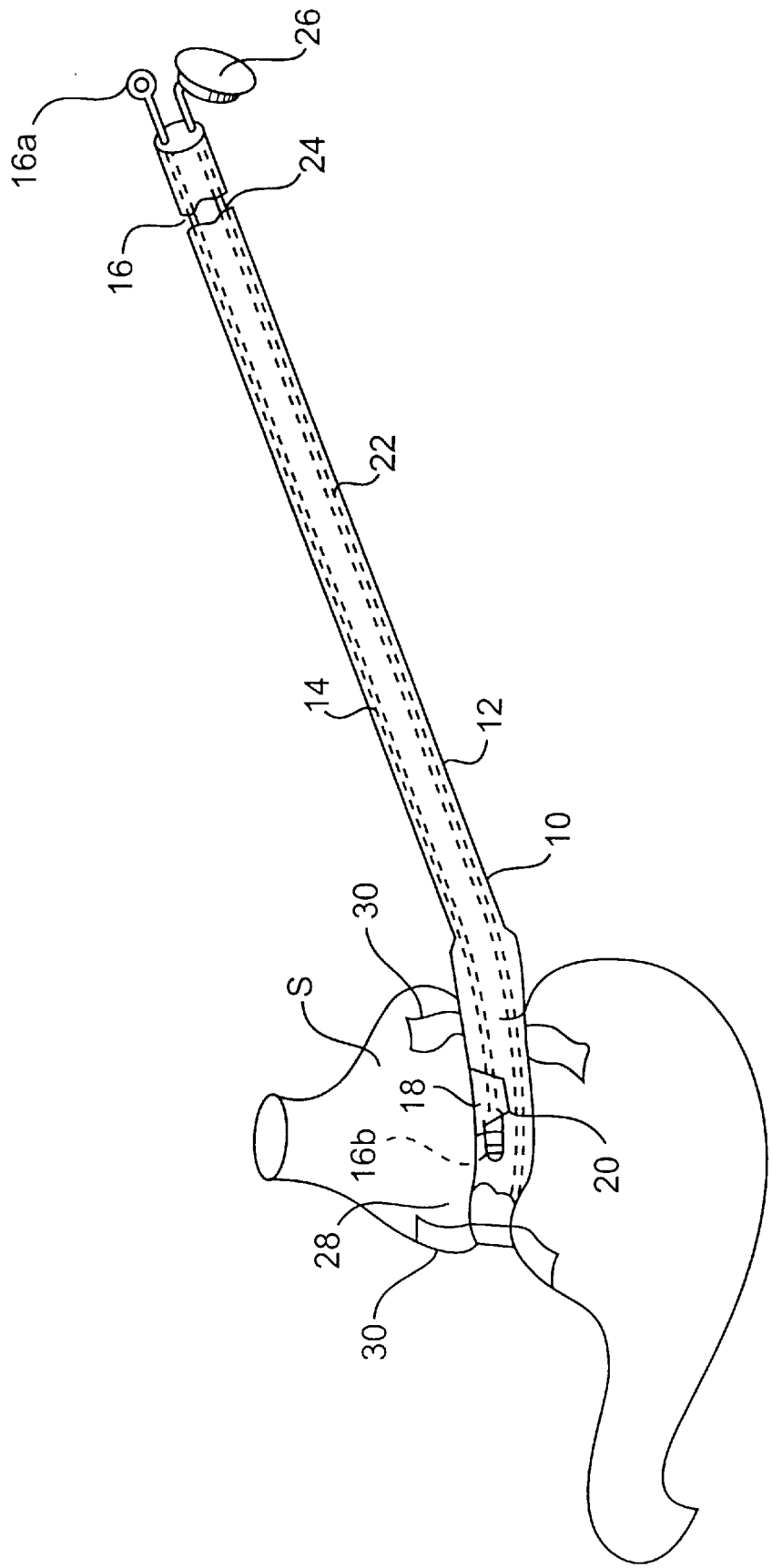
FIG. 1 is a highly schematic perspective view of a gastric banding device incorporating a holding means in accordance with a preferred embodiment of the invention.

Referring to FIG. 1, a gastric banding device, which is generally denoted 10, is shown in place around a stomach S. A banding device of the specific type shown in FIG. 1 is disclosed in my U.S. Pat. No. 5,449,368 (Kuzmak) which was mentioned above and which is hereby incorporated by reference. It will, of course, be appreciated that the present invention is not limited to use with this specific banding device and is applicable to other banding devices including those described in the patents listed above as well as to those described in other patents, e.g., U.S. Pat. No. 5,60,604 (Vincent).

Although reference is made to U.S. Pat. No. 5,449,368 (Kuzmak) for a more complete description thereof, in brief, device 10 comprises a band 12 which includes a loop or encircling portion (not fully visible in FIG. 1) that, in use, fully encircles the stomach S so as to form a stoma opening at the loop portion, thereby restricting food intake to the lower digestive portion of the stomach S below this loop portion. A first channel 14 formed in band 12 receives a control member 16 having an actuator loop 16a at one end and a locking bolt or screw 16b at the other. The locking bolt 16b extends through a locking element 18 provided at the free or distal end of band 14 and received in a corresponding shaped recess 20 formed in band 14 at an intermediate location therealong near the distal end so as to form the aforementioned loop portion. Locking screw 16b secures locking element 18 in recess 20 so as to fix the diameter of the loop portion of band 12 which encircles the stomach S.

A further channel 22 in band 12 receives an elongate tubular element 24 (or itself forms an elongate tubular passage) which is connected at one end at one end to a remote fill port or reservoir 26 and at the other end to a expandable section 28 which is provided on the inside face of the loop portion of band 12 that surrounds the stoma opening, i.e., on the stomach-facing surface of the loop portion. As described above, the effective diameter of the loop or encircling portion and hence the size of the stoma opening can be controlled by controlling the fluid supplied form the fill port or reservoir 26 to the expandable section 28.

Prior to the present invention, a band device such as device 10 would be sutured in place and/or the band device would be held in place by the adjacent stomach tissue which normally grows with the passage of time around and over the band to permanently anchor the band. However, as discussed above, these methods have not always been effective, thereby resulting in slippage or migration of the band. In accordance with the invention, there is provided one or more holding elements, generally denoted 30 in FIG. 1, for holding the band 12 in place and thereby preventing the band 12 from slipping or migrating.

Figure 2:
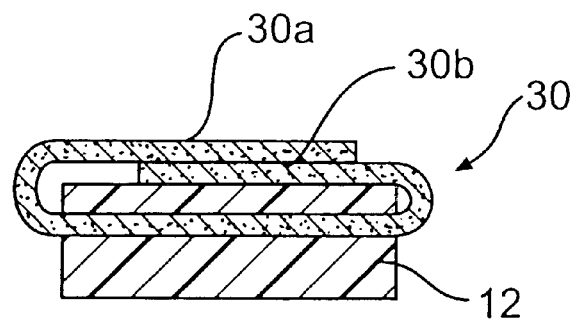
FIG. 2 is a transverse cross sectional view of one of the holding elements of the holding means of FIG. 1, as configured for insertion through a laparoscopic cannula.
Figure 3:
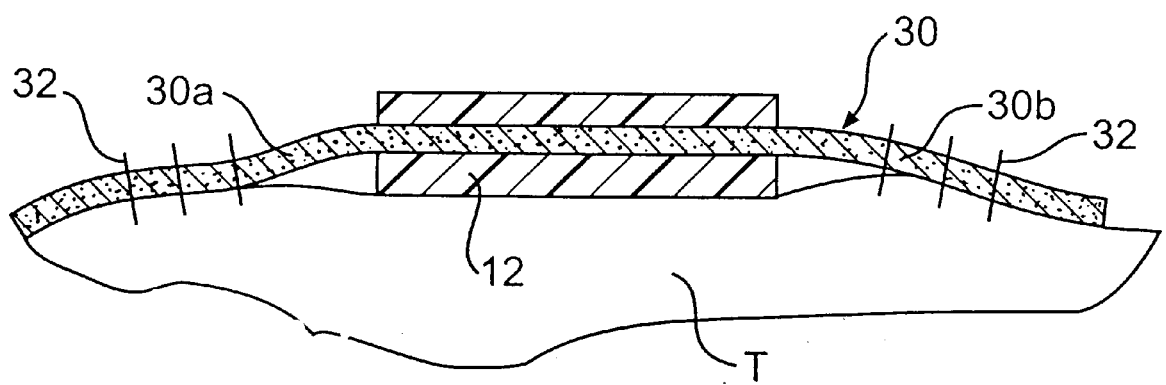
FIG. 3 is a transverse cross sectional view similar to that of FIG. 2 but showing the holding element in use.

As best seen in FIGS. 2 and 3, the holding elements 30 each comprise an elongate perforate or mesh member disposed transversely to the longitudinal axis of the band 14 and having outwardly extending end portions 30a and 30b. The holding element 30 is secured to band 12 by essentially being firmly embedded therein as shown in FIGS. 2 and 3 or by being affixed to a surface thereof or by any other means that will ensure that element 30 remains firmly connected to band 14.

Holding element 30 is particularly adapted for use with bands that are introduced laparoscopically into the body and, as shown in FIG. 2, for this purpose, the free ends 30a and 30b can be folded over, e.g., one on top of the other so as to only slightly increase the cross section the band 12 presented and thus not impede introduction of the band 12 down through the laparoscopic cannula. The mesh of the holding element 30 can be relatively rough and this may tend to hold the folded over end portions in place during the passage of the band 12 through the cannula, but depending on the flexibility of end portions 30a, 30b, and the nature of the material from which these portions are made, these portions will naturally stay in the folded over state. However, if necessary or desirable, a light adhesive or the like can be used to ensure this, and thus ensure that the ends 30a, 30b do not interfere with the passage of the band 12 through the cannula.

Once through the cannula, the holding element 30 is unfolded, i.e., the ends 30a, 30b are extended outwardly on both sides of the band 12. Thereafter the band 12 is secured in place as shown in FIG. 3, with the free ends 30a, 30b being secured to the tissue of the stomach S by suturing, as indicated by sutures 32. A major advantage of making at least these portions 30a, 30b out of a mesh material is that the tissue will in time grow through the mesh openings and serve to secure these ends 30a, 30b, and hence the band 12, firmly in place.

As shown in FIG. 1, multiple holding elements 30, spaced around the circumference of the looped portion of the band 12, can be provided to provide additional securing or holding force.

Although the present invention has been described relative to specific exemplary embodiments thereof, it will be understood by those skilled in the art that variations and modifications can be effected in these exemplary embodiments without departing from the scope and spirit of the invention.

What is claimed is:

1. In combination, a gastric band adapted for laparoscopic placement around the stomach of a patient so as to control the size of the stomach opening and holding means for holding said gastric band in place around the stomach, said gastric band comprising a band member having a proximal end and a distal end, means for affixing the distal end in place at an intermediate part of the band member so as to form a looped portion including an inner stomach-facing surface, a fluid reservoir, an inflatable member located on said inner surface, and fluid communication means, extending between said inflatable member and said distal end of said band member, for providing fluid communication between said inflatable member and said reservoir so as to enable inflation of said inflatable member from said reservoir, and said holding means being secured to said band member and including oppositely directed portions and extending transversely to said band member, said portions being movable between a first position wherein the holding means is used to hold the gastric band in place and wherein said portions extend beyond said band member on opposite sides thereof so as to enable said portions to be affixed to tissue adjacent to the band and a second position wherein the holding means and the band member are adapted to be inserted through a laparoscopic cannula and wherein said portions are brought close to the band member so as to decrease the cross sectional profile presented by the holding means and the band member.

2. The combination claimed in claim 1 wherein at least said free end portions of said holding element comprises perforate members.

3. The combination claimed in claim 1 wherein said holding means comprises a plurality of said holding elements.

4. In combination, a gastric band adapted for laparoscopic placement around the stomach of a patient so as to control the size of the stomach opening and holding means for holding said gastric band in place around the stomach, said gastric band comprising a band member having a proximal end and a distal end, means for affixed the distal end in place at an intermediate part of the band member so as to form a looped portion including an inner stomach-facing surface, a fluid reservoir, an inflatable member located on said inner surface, and fluid communication means, extending between said inflatable member and said distal end of said band member, for providing fluid communication between said inflatable member and said reservoir so as to enable inflation of said inflatable member from said reservoir, and said holding means comprising at least one elongate holding element secured to said band member and extending transversely to said band member, said at least one holding element including oppositely directed, perforate free end portions, said free end portions being movable between a first position wherein the holding element is used to hold the gastric band in place and wherein said free end portions extend, beyond said band member on opposite sides thereof so as to enable said free end portions to be affixed to the stomach of the patient and a second position wherein the holding element and the band member are adapted to be inserted through a laparoscopic cannula and wherein said free end portions are folded over onto the band member to decrease the cross sectional profile presented by the holding element and band member.

5. In combination, a gastric band adapted for laparoscopic placement around the stomach of a patient so as to control the size of the stomach opening and holding means for holding said gastric band in place around the stomach, said gastric band comprising a band member having a proximal end and a distal end, means for affixing the distal end in place at an intermediate part of the band member so as to form a looped band portion including an inner stomach-facing surface, a fluid reservoir, an inflatable member located on said inner surface, and fluid communication means, extending between said inflatable member and said distal end of said band member, for providing fluid communication between said inflatable member and said reservoir so as to enable inflation of said inflatable member from said reservoir, and said holding means comprising at least one elongate holding element secured to said band member and including oppositely directed, perforate free end portions extending transversely to said band member.

* * * * *